(12) United States Patent
Jochum

(10) Patent No.: US 6,416,460 B1
(45) Date of Patent: Jul. 9, 2002

(54) PENIS EXTENSION DEVICE

(76) Inventor: Herbert Jochum, Am Wallgraben 18, D-82541 Ammerland (DE)

(*) Notice: Subject to any disclaimer, the term of this patent is extended or adjusted under 35 U.S.C. 154(b) by 0 days.

(21) Appl. No.: 09/529,198

(22) PCT Filed: Sep. 29, 1998

(86) PCT No.: PCT/EP98/06164
§ 371 (c)(1), (2), (4) Date: May 31, 2000

(87) PCT Pub. No.: WO99/18897
PCT Pub. Date: Apr. 22, 1999

(30) Foreign Application Priority Data

Oct. 15, 1997 (DE) .......................... 197 45 611

(51) Int. Cl.⁷ ................................................ A61F 5/00
(52) U.S. Cl. ...................................................... 600/39
(58) Field of Search ................................... 600/38–41

(56) References Cited

U.S. PATENT DOCUMENTS 4,440,183 A    4/1984   Miller
5,599,275 A  * 2/1997   France ........................ 600/38
5,836,864 A  * 11/1998  Clark, Jr. .................... 600/38

FOREIGN PATENT DOCUMENTS

| DE | 296 02 101 | 6/1996 | |
|---|---|---|---|
| DE | 20020135 U1 * | 2/2001 | ................. 600/38 |
| FR | 1 605 238 | 8/1973 | |
| WO | WO 96 26691 | 9/1996 | |
| WO | WO 97 28764 | 8/1997 | |

* cited by examiner

*Primary Examiner*—Samuel G. Gilbert
(74) *Attorney, Agent, or Firm*—Katten Muchin Zavis Rosenman

(57) ABSTRACT

A penis extension device for enlarging the male member by long-term extension treatment of the corpora cavernosa comprises an extension element which runs between a fastening means (4), for securing the glans penis (5), and a support (2) which receives the penis root (3) and serves as an abutment. The extension element is designed as a flexible strap (1) which can be passed around the user's body.

8 Claims, 2 Drawing Sheets

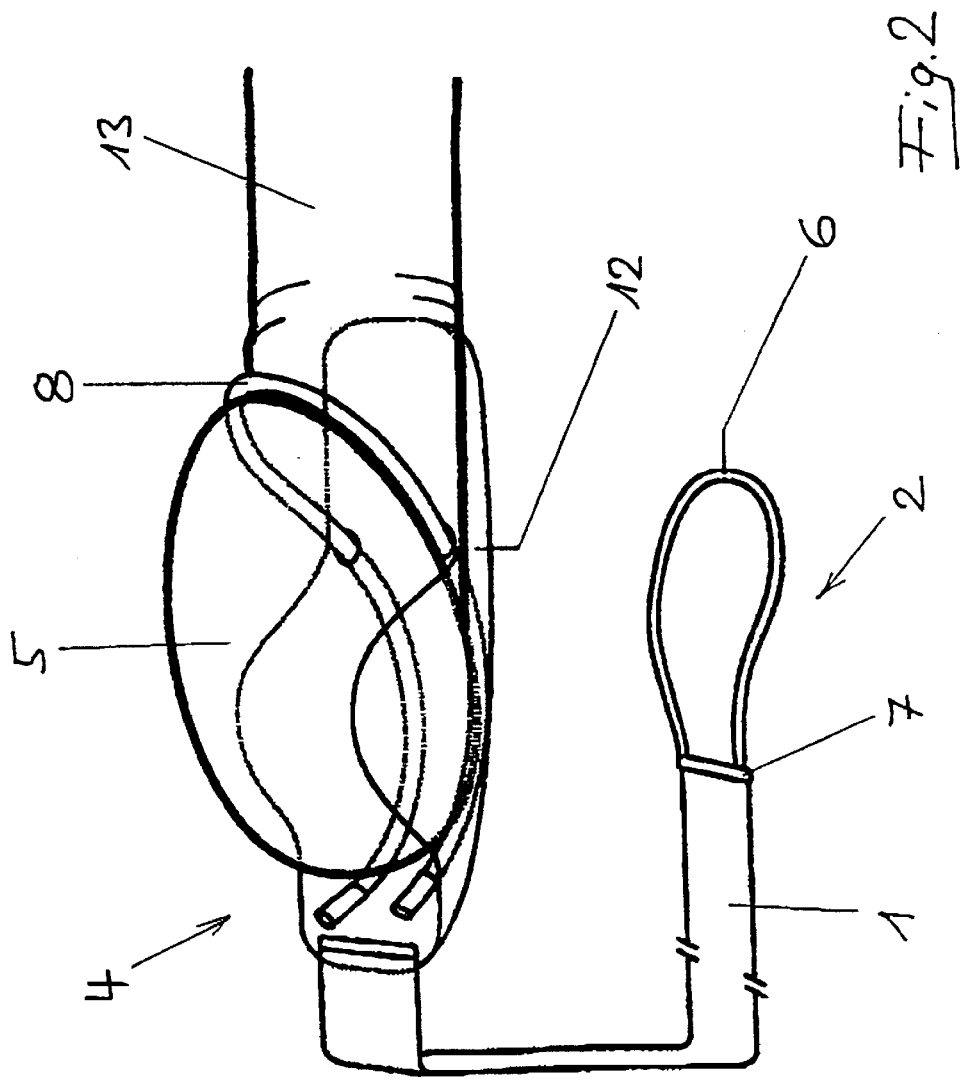

PENIS EXTENSION DEVICE

Figure 1:
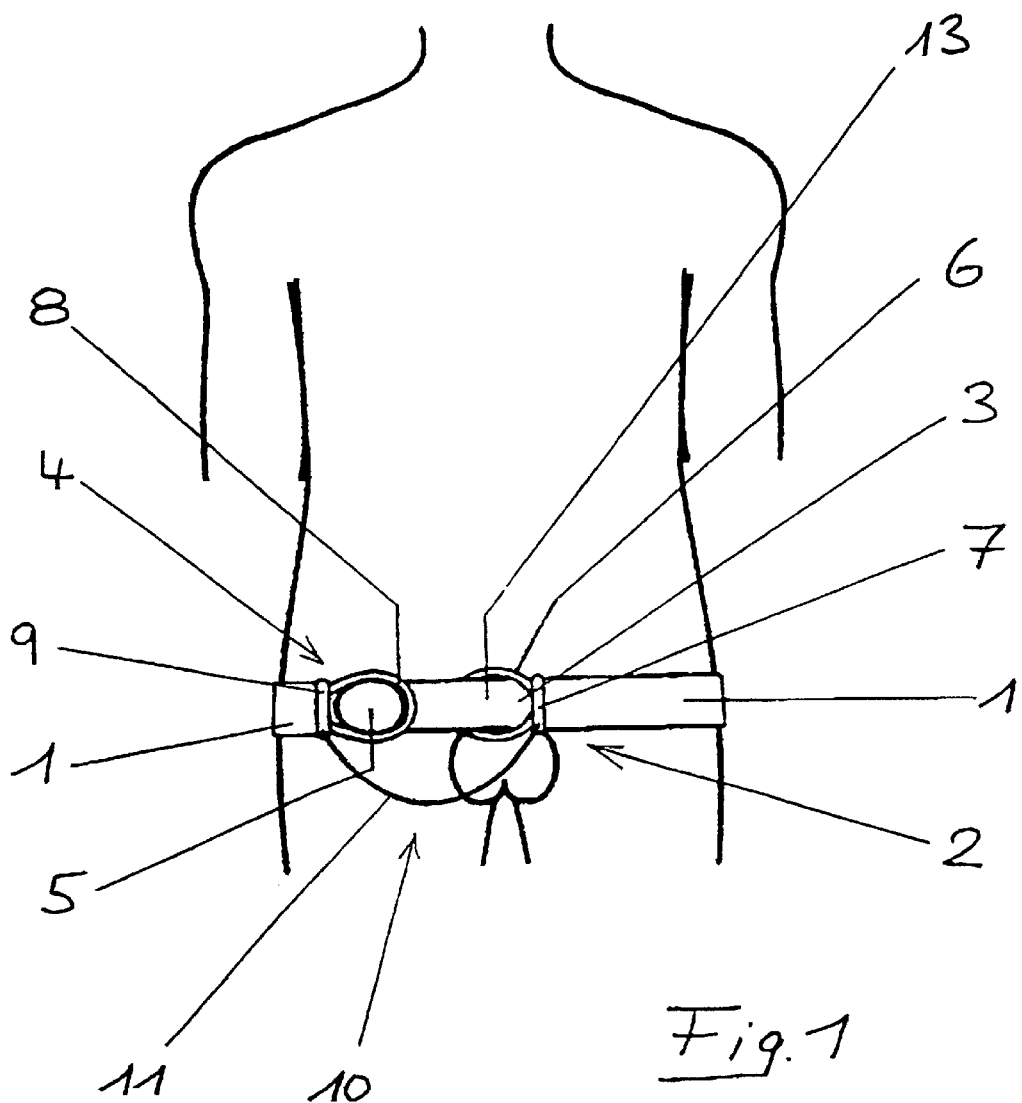

The present invention relates to a penis extension device for enlarging the male member by long-term extension treatment of the corpora cavernosa, comprising an extension element which runs between a releasable fastening means, for securing the glans penis, and a support which receives the penis root and serves as an abutment.

Men with too small a penis have two possible options at present. First, the penis can be surgically enlarged. Such an operation is extremely costly, however, and is not without its risk. Long-term extension treatment of the corpora cavernosa is also possible using devices of the type set out in the introduction. Such devices are disclosed in, for example, international patent applications WO96/26691 and WO97/28764 and German Utility Model 29602101. In the known penis extension devices, the extension element is always formed by two rods which run approximately parallel to the penis that is to be extended. These rods are supported on a ring or base plate which surrounds the penis in the area of the penis root. The length of the rods between, on the one hand, the ring serving as abutment and, on the other hand, the fastening means for securing the glans penis is adjustable (WO96/26691 and WO97/28764), in addition to which compression springs can be provided to generate prestressing (WO97/28764), or the fastening means for securing the glans penis can be moved on the rods and fixed at an individually selected position (DE 29602101 U1).

The known penis extension devices of the generic type have a number of serious disadvantages. The main one to be stressed here is that a discreet extension treatment of the corpora cavernosa is not possible. Instead, during treatment, the member to be extended is held out at up to 90° relative to the body by means of the known stretching mechanism. In addition, the stretching mechanism is by necessary longer than the member to be extended. As a consequence of this, it is in practice impossible to wear normal clothing during treatment. This in turn has the consequence that the known penis extension devices can in practice only be used at home or in private circles. This in turn leads to a relatively short period of daily use, which means an unsatisfactory result for the men in question.

Given the abovementioned disadvantages of known penis extension devices of the generic type, the object of the present invention is to make available a penis extension device which is of the type set out in the introduction and which can be worn discreetly.

According to the present invention, this object is achieved by the fact that the extension element is designed as a flexible strap which can be passed around the user's body. The configuration of the extension element according to the invention has the result that, during the extension treatment, the penis to be extended lies approximately sideward and close to the body of the person using the device according to the invention. This permits extension treatment under normal clothing, for which reason the treatment need not be restricted to times when the user finds himself in private; instead, it can be used discreetly for hours during the user's daily work schedule. A consequence of this is that regular use of the device according to the invention results in lasting extension of the penis after only a few months. The physical and emotional effect which such enlargement has on the man in question is enormous.

In addition to the advantages set out above, the penis extension device according to the invention involves a particularly small constructional outlay compared to generic devices of the prior art, which results in correspondingly low manufacturing costs.

In a first preferred development of the invention, the strap is elastically extensible. The strap can in this respect be designed in particular as a rubber strap. The elastic extensibility of the strap leads to a particularly effective and constant traction which continuously extends the member to be stretched and thus promotes its gradual enlargement.

In a further preferred development of the invention, the strap can be adjusted in length. By shortening or lengthening the strap, the penis extension device according to the invention can be adapted to the girth of the user's body. In addition, the force with which the member is stretched can be adjusted in this way.

In a further preferred development of the invention, the support for the penis root is designed as an annular cuff. At the start of each extension treatment, this annular cuff, to which the strap can be secured at one end, is pushed along the penis as far as the root. The strap is then placed around the user's body and the glans penis is secured on the fastening means. The annular cuff ensures that the counter-force to the traction force exerted on the glans penis is led to the penis root, so that there is a closed system of forces.

The fastening means for the glans penis can preferably comprise a saucer-shaped slide. In this case, a small loop-shaped band can in particular be provided with which the glans penis can be secured on the slide.

In a further development of the penis extension device according to the invention, a holder element is provided which runs between, on the one hand, the support for the penis root and/or that end of the strap assigned thereto and, on the other hand, the fastening means for the glans penis and/or that end of the strap assigned thereto. This holder element, which can be designed for example as a non-extensible string, is relaxed during use as intended of the penis extension, device. It comes into operation when the user releases the attachment of the glans penis on the fastening means, for example in order to pass water. In this case, the holder element prevents the fastening means from snapping against the user's back under the traction of the elastically extensible strap. The holder element is so dimensioned that it holds the fastening means, released from the glans penis, on the side of the user's hip, so that renewed securing of the glans penis can be done without any problem. In addition, the holder element prevents the penis extension device from slipping down when its user is wearing it as it were on "standby", without in actual fact carrying out any extension treatment.

The present invention is explained in greater detail below on the basis of two preferred illustrative embodiments which are represented in the drawing, in which:

FIG. 1 shows an overall view of a first preferred embodiment of the penis extension device according to the invention during correct use thereof; and FIG. 2 shows a particularly preferred design of the fastening means for securing the glans penis.

The penis extension device shown in FIG. 1 comprises an elastically extensible, flat strap 1, at one end of which there is fastened a support 2 for the penis root 3 and, at its other end, a fastening means 4 for securing the glans penis 5. The support 2 for the penis root 3 is designed as an annular cuff 6, the connection to the strap 1 being effected via a clamping element 7 across the entire width of the strap. The fastening means 4 for securing the glans penis 5 comprises a loop-shaped small band 8, both ends of which are fixed to a clamping element 9 which is in turn secured on the second end of the strap 1. Running between the two clamping elements 7 and 9 there is a holder element 10 in the form of a string 11 which hangs loosely during correct use of the penis extension device and is only used when the fastening means 4 is released from the glans penis 5. The string 11 is attached in a releasable manner to one of the two clamping elements 7 and 9; the connection here is only made once the strap 1 has been passed around the user's body.

FIG. 2 shows in perspective representation that the fastening means 4 securing the glans penis 5 can comprise a saucer-shaped slide 12 which, from underneath, partially surrounds the glans penis 5 and the front end of the body 13 of the penis. The slide 12 is firmly connected to one end of the strap 1. The two ends of the small band 8, with which the glans penis is secured on the slide, are connected to it.

What is claimed is:

1. A penis extension device for enlarging the male member by long-term extension treatment of the corpora cavernosa, comprising:

an extension element which runs between a fastening means, for securing the glans penis, and a support, which is adapted to receive the penis root and serves as an abutment, wherein the extension element is designed as a flexible strap which is adapted to be passed around a user's body.

2. The penis extension device as claimed in claim 1, wherein the strap is elastically extensible.

3. The penis extension device as claimed in claim 1, wherein the strap is length-adjustable.

4. The penis extension device as claimed in claim 1, wherein the support for the penis root is designed as an annular cuff.

5. The penis extension device as claimed in claim 1, wherein the fastening means for the glans penis comprises a slide.

6. The penis extension device as claimed in claim 5, wherein the fastening means further comprises a small band for securing the glans penis on the slide.

7. The penis extension device as claimed in claim 5, wherein the slide is saucer-shaped.

8. The penis extension device as claimed in claim 1, wherein a holder element is provided which runs between the support for the penis root and the fastening means for the glans penis.

* * * * *